United States Patent [19]
Inoue et al.

[11] Patent Number: 5,930,033
[45] Date of Patent: Jul. 27, 1999

[54] SLIT SCAN CENTRIFUGE MICROSCOPE

[75] Inventors: Shinya Inoue, Falmouth, Mass.; Keisuke Suzuki, Yokohama, Japan

[73] Assignees: Marine Biological Labortory, Hole, Mass.; Olympus Optical Co., Ltd., Tokyo, Japan

[21] Appl. No.: 08/910,109

[22] Filed: Aug. 13, 1997

[51] Int. Cl.⁶ .................. G02B 21/06; G02B 26/02
[52] U.S. Cl. .................. 359/368; 359/234; 359/385
[58] Field of Search .................. 359/368–390, 359/227–236, 900; 250/234–236, 559.37, 206.1, 566, 306–310; 425/143, 425; 422/72, 73, 81, 58, 102–103; 356/28, 28.5, 39, 73, 427

[56] References Cited

U.S. PATENT DOCUMENTS

| | | | |
|---|---|---|---|
| 2,164,526 | 7/1939 | Kimmich | 359/234 |
| 3,435,213 | 3/1969 | Colbow et al. | 359/233 |
| 4,158,502 | 6/1979 | Greiner et al. | 359/233 |
| 5,162,941 | 11/1992 | Favro et al. | 359/368 |
| 5,177,512 | 1/1993 | Abe et al. | 359/368 |
| 5,528,027 | 6/1996 | Mizutani | 250/234 |
| 5,619,371 | 4/1997 | Pontius | 359/368 |

FOREIGN PATENT DOCUMENTS 63-250615  10/1988  Japan.

*Primary Examiner*—Thong Nguyen
*Attorney, Agent, or Firm*—Pillsbury Madison & Sutro LLP

[57] ABSTRACT

A centrifuge microscope that includes: a rotary disk in which are provided a slit and a sample chamber; a light source for illumination; a projecting optical system; and an objective lens. The projecting optical system includes an imaging lens, a pair of reflecting mirrors, and a projecting lens which are constructed and arranged such that an erect image or an inverted image of the slit is projected on a sample contained in the sample chamber. During rotation of the rotary disk, the slit image and the sample sweep by each other in front of the objective lens, whereby the sample can be observed via the objective lens as a still image having better definition.

17 Claims, 12 Drawing Sheets

MOVING DIRECTION OF SLIT IMAGE

MOVING DIRECTION OF SAMPLE

SAMPLE IMAGE
BEFORE CORRECTION

SAMPLE IMAGE
AFTER CORRECTION

FIG. 12   MOVING DIRECTION OF SLIT IMAGE
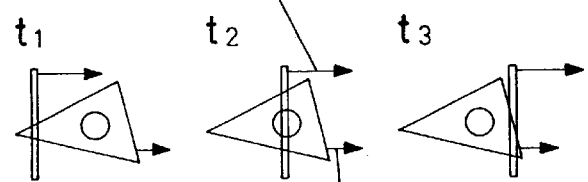
MOVING DIRECTION OF SAMPLE
FIG. 13A
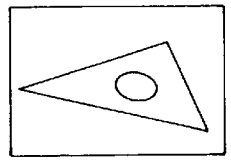
SAMPLE IMAGE
BEFORE CORRECTION
FIG. 13B
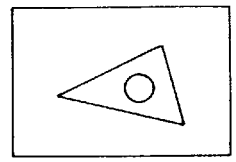
SAMPLE IMAGE
AFTER CORRECTION

SLIT SCAN CENTRIFUGE MICROSCOPE

BACKGROUND OF THE INVENTION a) Field of the Invention

The present invention relates to a microscope, specifically to that allowing one to observe a sample under centrifugal force.

b) Description of the Related Art

There are several types of centrifuge microscopes, which allow observation of a sample under centrifugal force. A stroboscopic centrifuge microscope is one of these types (Refer to Japanese Patent Preliminary Publication No. Sho 63-250615). In this type of centrifuge microscope, a sample chamber is arranged on a rotary disk such as to cross the optical axis of an objective lens in accordance with the rotation of the rotary disk. The microscope causes a pulse-emitting light source to emit pulsed light of very short duration at instants when the sample is carried in front of the objective lens by controlling the timing of the flashes given off by the light source based only on the position of the sample chamber as detected during the rotation of the disk, so that a still image of the sample is observed in spite of the revolving movement of the sample chamber.

In this type of centrifuge microscope, however, the timing of pulse emission can vary each time the sample is carried in front of the objective lens because of the jitter in the pulse-emitting light source, and thus the position of the image in the visual field does not remain stationary, which causes the image to blur and thus is unfavorable. Furthermore, since the emission timing is controlled relying only on positional detection of the sample chamber arranged on the disk, the emission of pulsed light is not completely synchronized with the event of the sample coming in front of the objective lens when the rotational speed of the disk is being changed, and precludes observation during such changes.

SUMMARY OF THE INVENTION

An object of the present invention is to provide a centrifuge microscope with good resolution through which the sample image is free from blur and through which observation is not precluded even when the rotational speed of the rotary disk is in the midst of change.

In order to attain this object, a centrifuge microscope according to the present invention includes a light source, a slit which is positioned in the light beam emergent from the light source, an objective lens, a rotary disk which is provided with a sample chamber arranged such as to cross the optical axis of the objective lens in accordance with the rotation of the rotary disk, and a projecting optical system for projecting the image of the slit on the sample which is contained in the sample chamber, the position of the slit image which is projected by the projecting optical system on the sample in front of the objective lens being changed relative to the position of the sample in accordance with the rotation of the rotary disk.

According to the present invention, the slit is arranged in the rotary disk and the projecting optical system is configured to project the slit image on the sample as an erect image or an inverted image.

According to the present invention, the projecting optical system includes at least one reflecting mirror, the reflecting mirror being constructed such that the position of the slit image is adjustable thereby.

Also, a centrifuge microscope according to the present invention includes a light source for illumination, an objective lens, a rotary disk provided with a sample chamber and a slit, the sample chamber being arranged such as to cross the optical axis of the objective lens in accordance with the rotation of the rotary disk and the slit being arranged such as to cross a light beam from the light source in accordance with the rotation of the rotary disk, and a projecting optical system for projecting the slit image on the sample which is contained in the sample chamber, the slit image formed by the projecting optical system being associated with the sample such that they move in directions opposite to or parallel to each other during the rotation of the rotary disk and sweep by each other in front of the objective lens intermittently. Here, "intermittently" is directed to a situation where the slit image and the sample sweep by other each time the sample is carried in front of the objective lens during the rotation of the rotary disk. They can "sweep by each other" either in a situation where they move in directions opposite to each other or in a situation where they move in parallel directions with one outpacing the other. During the "sweeping", the slit image is kept superimposed on at least one part of the sample.

This and other objects as well as the features and the advantages of the present invention will become apparent from the following detailed description of the preferred embodiments when taken in conjunction with the accompanying drawings.

BRIEF DESCRIPTION OF THE DRAWINGS

FIG. 12 illustrates a process in which the slit image and the sample move in parallel directions;

FIGS. 13A and 13B show a sample image as obtained by the microscope shown in FIG. 10 (i.e. before correction) and a sample image after correction, respectively;

DETAILED DESCRIPTION OF THE PREFERRED EMBODIMENTS

Figure 1:
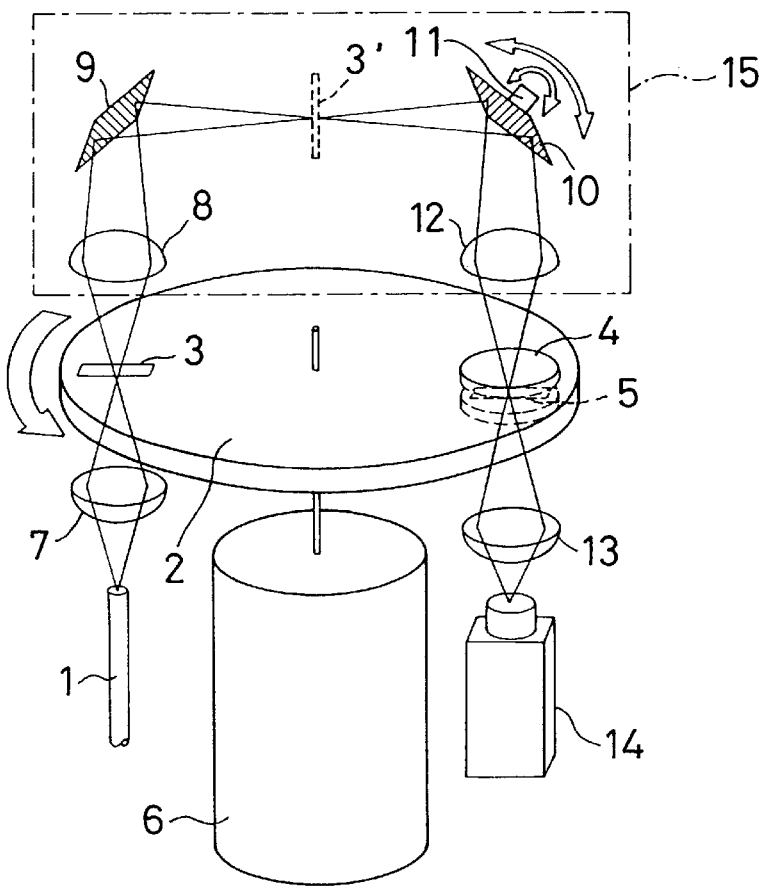
FIG. 1 is an overall view showing an optical system in an erect-image-mode slit scan centrifuge microscope according to the present invention.

The preferred embodiments of the present invention are described below with reference to the drawings, in which like reference symbols indicate members or portions of the members having like functions.

First, a configuration of a microscope according to one embodiment of the present invention is described with reference to FIG. 1. A light source 1, in which an optical fiber unit for transmitting light may be incorporated, is arranged to provide the illumination. A rotary disk (rotary centrifuge disk) 2 is provided with a slit 3 and a transparent sample chamber 4. The slit 3 is formed on one side of a diameter of the rotary disk 2 and extends in a direction of the diameter, while the transparent sample chamber 4 is arranged on the opposite side of the same diameter. The sample chamber 4 contains a sample 5. A motor 6 is arranged for rotating the rotary disk 2. The illumination light from the light source 1 is projected on the rotary disk 2 by a lens 7, to pass through the slit 3. An imaging lens 8 forms an intermediate image 3' of the slit 3. A reflecting mirror 9 bends a beam of the illumination light at right angles. A reflecting mirror 10 further bends the beam substantially at right angles. An adjusting device 11 makes the reflecting mirror 10 slightly pivotal along two axes intersecting on a point at the center of the the mirror 10, as indicated by the double-headed arrows in FIG. 1. A projecting lens 12 projects the intermediate image 3' of the slit 3 on the sample 5 which is contained in the sample chamber 4. An objective lens 13 of the microscope and a video camera 14 are arranged to allow an observer to view an image of the sample. The imaging lens 8, the reflecting mirrors 9, 10 and the projecting lens 12 form the projecting optical system 15. As the drawing shows, the light source 1 and the projecting optical system 15 lie stationary outside of the space occupied by the rotary disk 2.

Figure 2A:
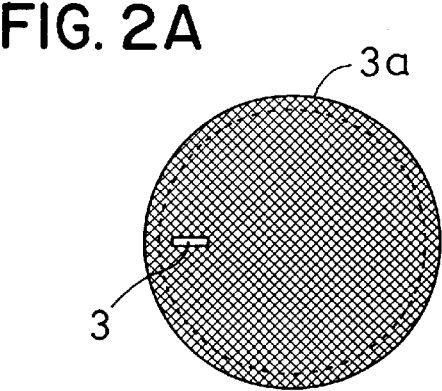
FIGS. 2A and 2B are a top plan view and a side view, respectively, of a glass base plate to which a coating is applied by evaporation to form a slit.
Figure 2B:

As shown in FIG. 2A, an aluminum film is coated on a glass base plate 3a by evaporation such as to form the slit 3 using a lithographic technique. As shown in FIG. 2B, the circumference of the glass base plate 3a has an inclined face. The coating of the aluminum film is applied to the larger-area-side, or bottom surface of the glass base plate 3a except one portion, which forms the slit 3 for transmitting light therethrough. The width of the slit 3 is set such that its image projected on the sample 5 is smaller than the resolving power of the objective lens 13.

Figure 3A:
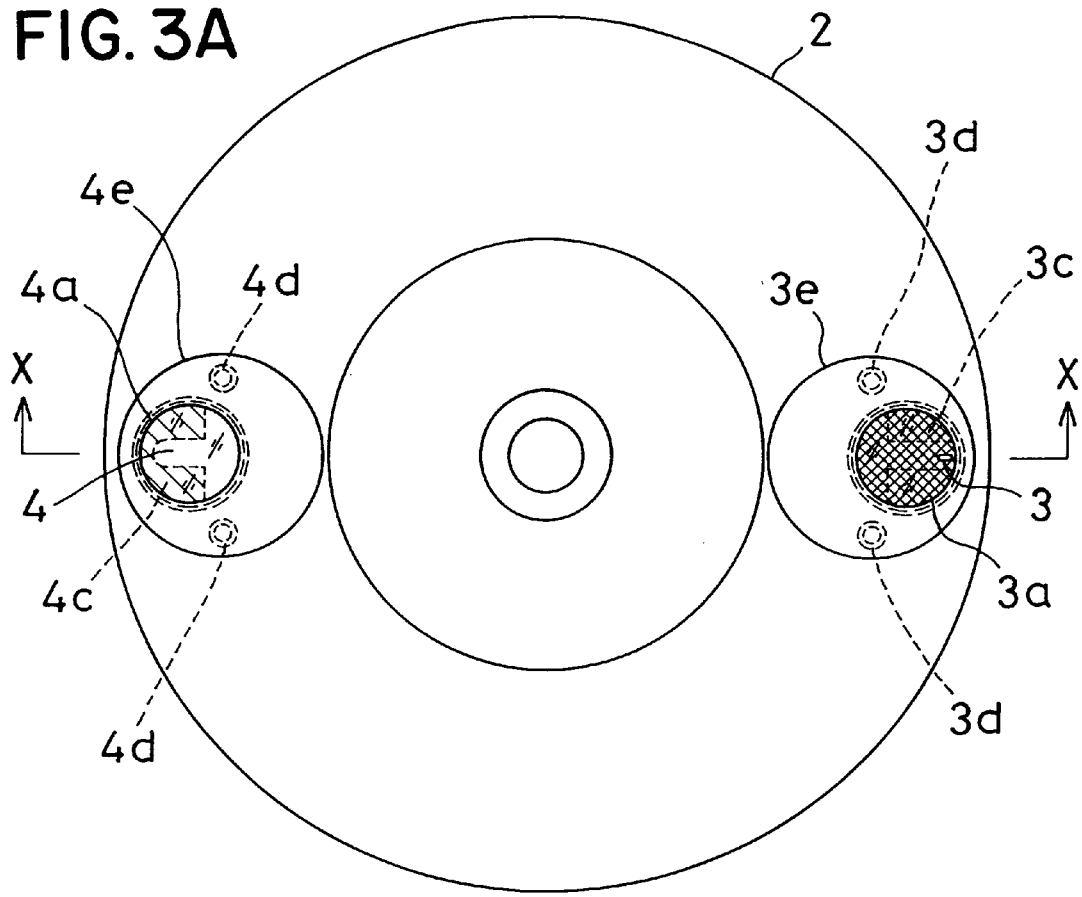
FIG. 3A is a plan view illustrating the detailed structure of a rotary disk appearing in FIG. 1.
Figure 3B:
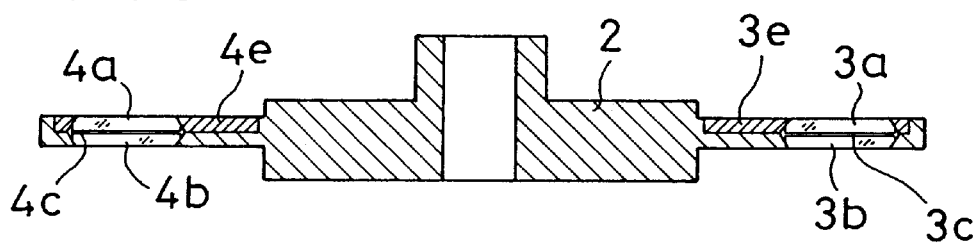
FIG. 3B is a sectional view of the rotary disk taken across a line X—X of FIG. 3A.

As illustrated in FIGS. 3A and 3B, the glass base plate 3a in which the slit 3 is thus formed is made immovable with respect to the rotary disk 2 by a member 3e which is afixed to the rotary disk 2 with screws 3d, upon being mated with a glass base plate 3b, which is shaped congruent with the glass base plate 3a but has no evaporation film on it, such that the glass base plates 3a and 3b face each other bottom-to-bottom with intervention of a spacer 3c.

Figure 3C:
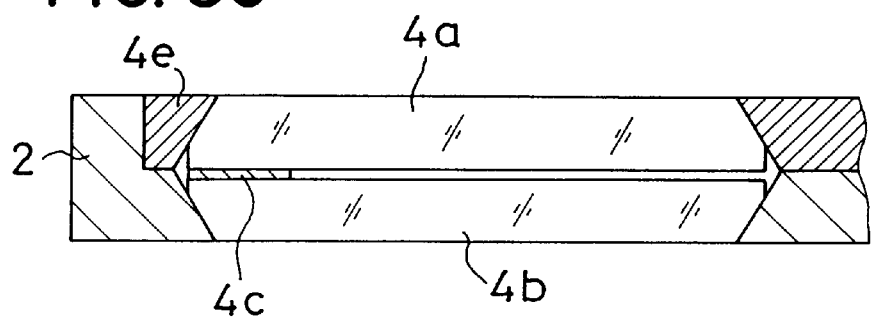
FIG. 3C is an enlarged view of a sample chamber appearing in FIG. 3B.

As illustrated in FIGS. 3A, 3B and 3C, the sample chamber 4 is formed of two congruently-shaped glass base plates 4a, 4b which are arranged to face each other with intervention of an opaque spacer 4c. The sample chamber 4 is made immovable with respect to the rotary disk 2 by a member 4e which is fixed to the rotary disk 2 with screws 4d. As illustrated in FIG. 3A, the spacer 4c shows a U-shaped opening when viewed from the top. The sample 5 is placed in this U-shaped transparent space.

To facilitate assembly, it is preferred that each pair of the glass base plate combinations 3a–3b, 4a–4b and the fixing members 3e, 4e be mutually congruently shaped to be replaceably fitted in place, with the screws 3d, 4d also being mutually congruently shaped to be replaceably used.

From the simplified drawing of FIG. 1, it would seem that the positions of the slit 3 and the sample 5 are symmetric about the center of the rotary disk 2. However, in reality, the slit 3 is formed to be deviated from the center of the glass base plate 3a and thus the positions of the slit 3 and the sample 5 are not symmetric about the central axis of the rotary disk 2 when they are set in place in the rotary disk 2 as illustrated in FIG. 3A.

The sample 5 is inserted in the U-shaped space formed by the opaque spacer 4, on which space the image of the slit 3 is designed to be projected. Since the center of the sample chamber 4 lies in the U-shaped space and, at instants when the rotary disk 2 is in a position shown in FIG. 1, is substantially aligned with the optical axis of the objective lens 13, the sample 5 in the U-shaped space can be observed through the slit image projected.

When the rotary disk 2 is rotated by 180° from the position shown in FIG. 1 to carry the slit 3 in front of the objective 13, light from the light source 1 is intercepted by the base of the U-shaped opaque spacer 4c which is now located at a position where the slit 3 previously existed. As a result, during rotation of the rotary disk 2, the light from the sample 5 is introduced into the camera 14 only when the actual sample 5 and the image of the slit cross the space in front of the objective lens 13. If the spacer 4c were made of a transparent material, unwanted light from the light source 1 would pass through the sample chamber 4 and reach the camera 14 at instants when the slit 3 crosses the space in front of the objective lens 13, to preclude observation of a good image.

Figure 4:
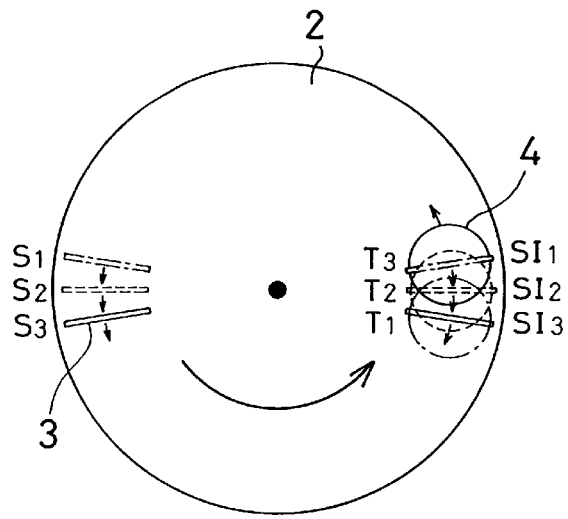
FIG. 4 illustrates the positional relationship between a sample which is arranged in the rotary disk and a slit image which is projected as an erect image by a stationary optical system such as shown in FIG. 1.

Next, the function of the above-described apparatus will be explained. FIG. 1 shows a state where the beam of illumination light from the light source 1 is transmitted through the slit 3 to be projected as an erect image of the slit 3 on the sample 5 via the projecting optical system 15. As shown in FIG. 4, in the course that the rotary disk 2 is driven by the motor 6 to rotate counterclockwise (as indicated by the single-headed arrow in FIG. 1), the slit 3 and the sample chamber 4 are shifted counterclockwise in orders of $S_1$, $S_2$, $S_3$ and $T_1$, $T_2$, $T_3$, respectively, while the erect image of the slit 3 is shifted in an opposite direction (i.e. clockwise) in order of $SI_1$, $SI_2$, $SI_3$ because the slit image is first formed as an intermediate image 3' and then projected on the sample 5. Consequently, during the rotation of the rotary disk 2, the sample 5 sweeps by the image of the slit 3 intermittently in front of the objective lens 13. Here, "intermittently" is directed to a situation where the image of the slit 3 and the sample 5 sweep by each other each time the sample 5 is carried in front of the objective 13 during the rotation of the rotary disk 2. In this embodiment, the slit image and the sample 5 change their positions relative to each other and "sweep by each other" in moving in directions opposite to each other. In the scope of the present invention, however, a slit image and a sample may also sweep by each other where they move in parallel directions, with one outpacing the other. While the slit image and the sample 5 are "sweeping each other", the slit image is superimposed on at least one part of the sample 5.

As a result, the sample 5 in the sample chamber 4 under centrifugal force is exposed to the illumination light for a time period through which the projected slit image is sweeping the sample 5. This operation corresponds to high-speed release of a camera shutter; a still image can be observed even for a sample which is moving at a high speed.

Since a positional relationship between the slit 3 and the sample 5 is fixed in the rotary disk 2, the image of the slit 3 is constantly projected on definite portions on the sample 5 each time the slit 3 is inserted in the beam of the illumination light. As a result of such a good synchronization, a still image of the sample 5, which is obtained through the high-speed relative movement between the sample 5 and the slit image in front of the objective lens 13, maintains its stability; this configuration is free from the jitter inherent in a conventional pulsed light source or the asynchronizm which would occur in the midst of change of rotational speed of the rotary disk.

The foregoing descriptions of this embodiment are based on a supposition that the projecting optical system 15 projects a full-scale image of the slit 3 on the sample 5. However, the projecting optical system 15 may be constructed to project an enlarged slit image on the sample 5. In this case, relative moving speed of the image of the slit 3 projected on the sample 5 with respect to the sample 5 is higher for the increased projection magnification. This causes the time taken for the slit image to completely sweep the sample 5, or "exposure time" to be shortened, and thus a still image of the high-speed revolving sample is obtained with better definition.

Figure 5:
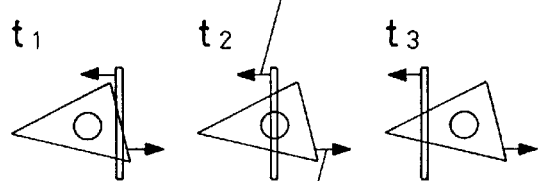
FIG. 5 illustrates a process in which the slit image and the sample move in mutually opposite directions.
Figure 6A:
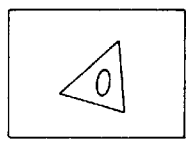
FIGS. 6A and 6B show a sample image as obtained by the microscope shown in FIG. 1 (i.e. before correction) and a sample image after correction, respectively.
Figure 6B:
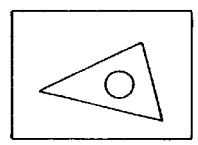
Figure 7:
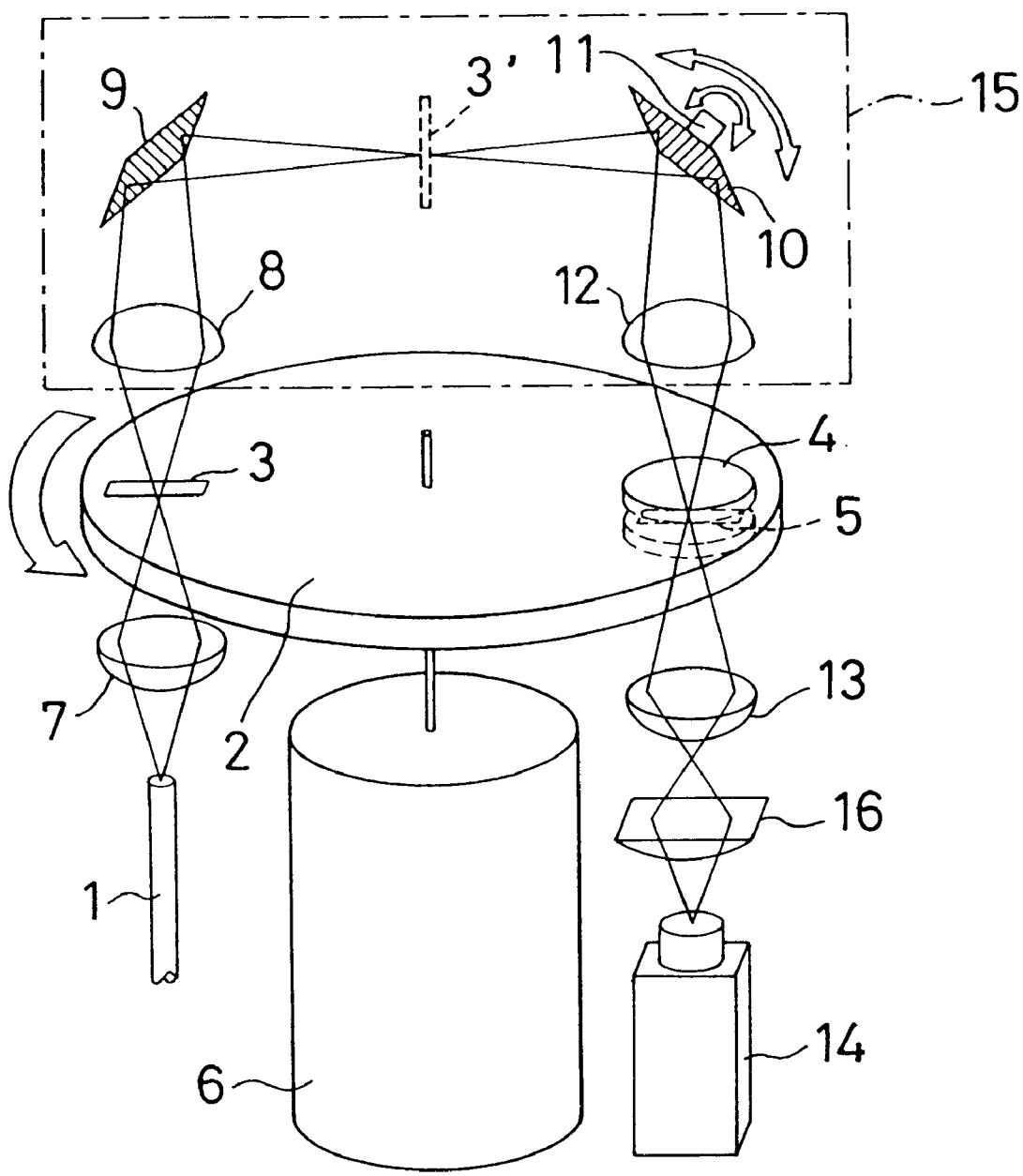
FIG. 7 is an overall view of a modification of the microscope shown in FIG. 1 wherein an anamorphic optical system is employed for correcting the sample image.
Figure 8:
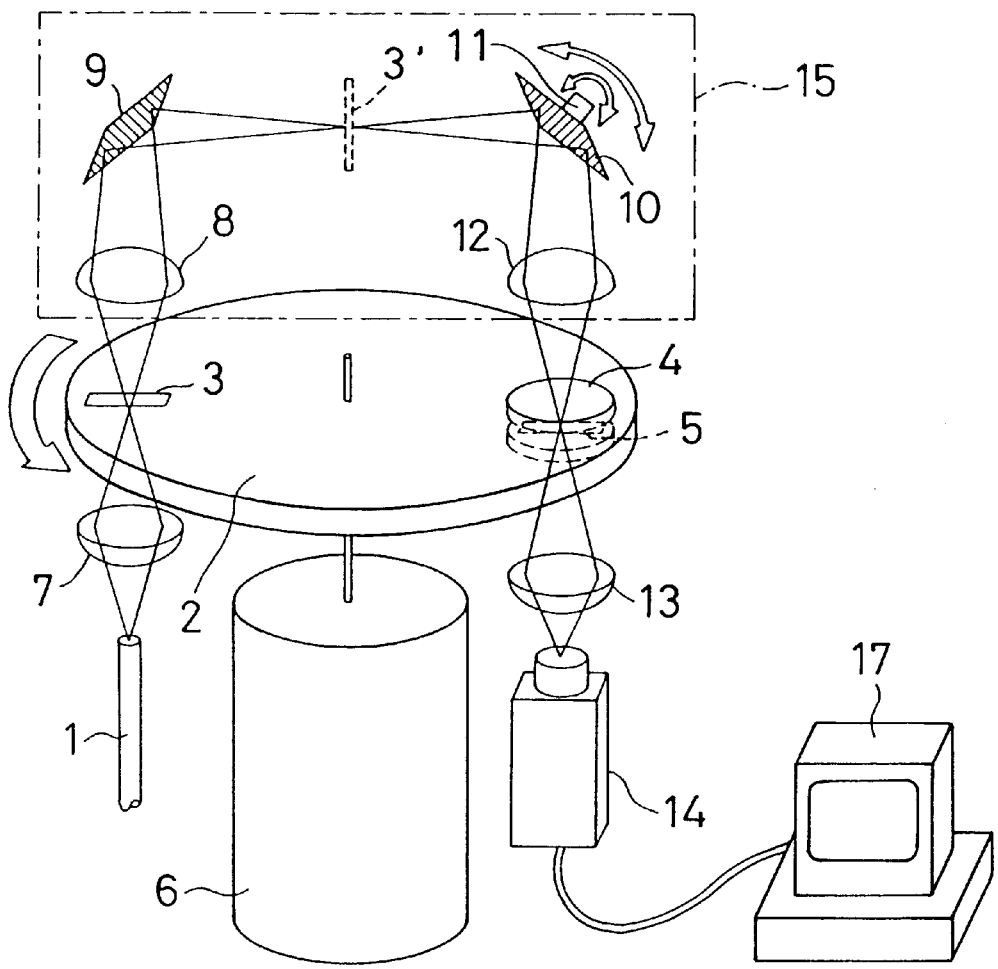
FIG. 8 is an overall view of another modification of the microscope shown in FIG. 1 wherein a means for image processing is added to correct the sample image.

FIG. 5 schematically shows a process in which the slit image and the sample 5 move in mutually opposite directions to sweep each other. Time elapses in order of $t_1$, $t_2$, $t_3$. If the slit image and the sample 5 move in mutually opposite directions at the same speed to sweep by each other, a sample image for observation is obtained compressed to one half only in the moving direction of the slit image or the sample 5 (i.e. tangent direction to the rotary disk 2) in reference to the original aspect ratio of the sample 5, as shown in FIG. 6A. The degree of compression depends on the relationship in speed between the slit image and the sample 5. This one-directionally reduced image can be optically transformed to have the original aspect ratio of the sample 5, as shown in FIG. 6B, by the use of an anamorphic optical system 16 which has different powers for X and Y directions and is positioned between the objective lens 13 and the camera 14, as shown in FIG. 7. Alternatively, the sample image may be electrically corrected by an image processor 17 which is connected to the camera 14, as shown in FIG. 8, to be displayed as an appropriately expanded image at a video sensor or a display.

According to this embodiment, the light beam passing through the slit 3, which is arranged in the rotary disk 2, is led to the sample 5, which is arranged in the same rotary disk 2, as the slit image by a pair of reflecting mirrors 9, 10. The reflecting mirrors 9, 10, however, may be replaced by a roof prism, which can perform the same function. Similarly, a single reflecting mirror can be arranged instead of the pair of reflecting mirrors 9, 10.

Figure 9:
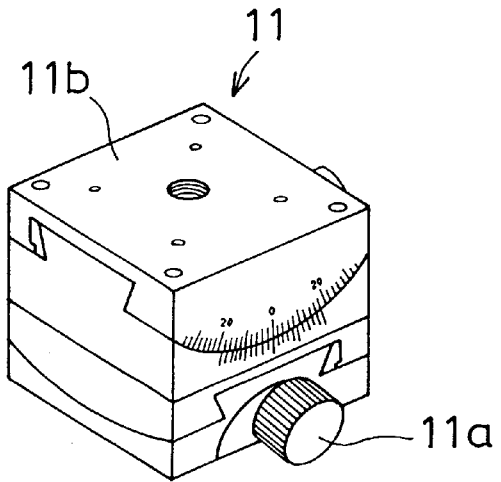
FIG. 9 is an oblique view of a goniostage, which is an example of the adjusting devices.

Since the adjusting device 11 allows the reflecting mirror 10 to pivot slightly around a point on the central axis of the mirror 10, the slit image can be located at an optimum portion of the sample 5. FIG. 9 shows one example of the adjusting device 11. The device shown in the figure is generally referred to as a goniostage, where a stage 11b is rotated about the XY axes by turning a pair of control knobs 11a (only one appears in the figure). The reflecting mirror 10 is mounted on the stage 11b.

Furthermore, for the purpose of assuring the slit image to remain in focus on the sample 5, the above-described microscope may be constructed such that the rotary disk 2 or the entire projecting optical system 15 is movable along the axis of the motor 6, or such that a part of lenses are movable along its optical axis.

The foregoing descriptions of one embodiment of the present invention show that a still image of the revolving sample can be observed with better definition via the objective lens where the sweeping image of the slit is projected on the sample as an erect image by the projecting optical system to move in a direction opposite to the moving direction of the sample.

On the other hand, the present invention is applicable to a case where the slit image is projected on the sample as an inverted image by the projecting optical system; a similar effect can be obtained with such an arrangement also. The following descriptions are directed to one embodiment of the present invention in which an inverted image of the slit is used. First, an overall configuration of this embodiment is described in reference to FIG. 10.

Figure 10:
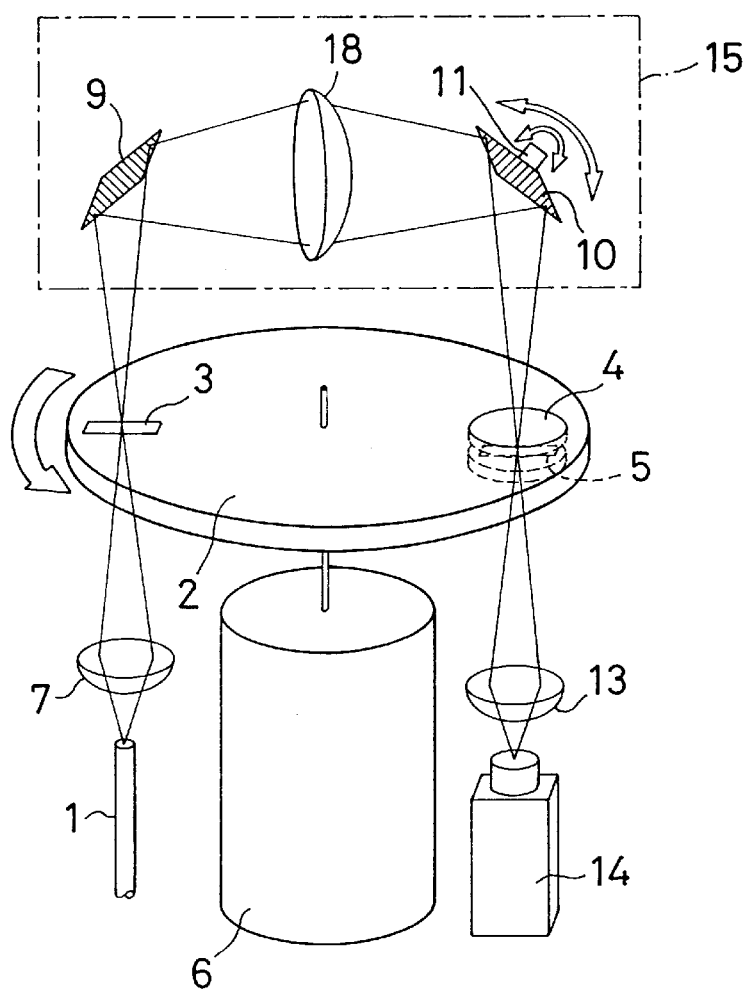
FIG. 10 is an overall view showing an optical system of an inverted-image-mode slit scan centrifuge microscope according to the present invention.

The FIG. 10 embodiment differs from the above-detailed embodiment in that the projecting optical system 15 directly projects an inverted image of the slit 3 on the sample 5 without forming an intermediate image such as shown in FIG. 1. Specifically, according to the embodiment shown in FIG. 10, a projecting optical system 15 is constructed to be an enlarging optical system which includes a reflecting mirror 9, a lens 18 for projecting the slit image directly on the sample 5 in a sample chamber 4, and a reflecting mirror 10, while remaining sections of this apparatus are configured same as the embodiment in FIG. 1.

Figure 11:
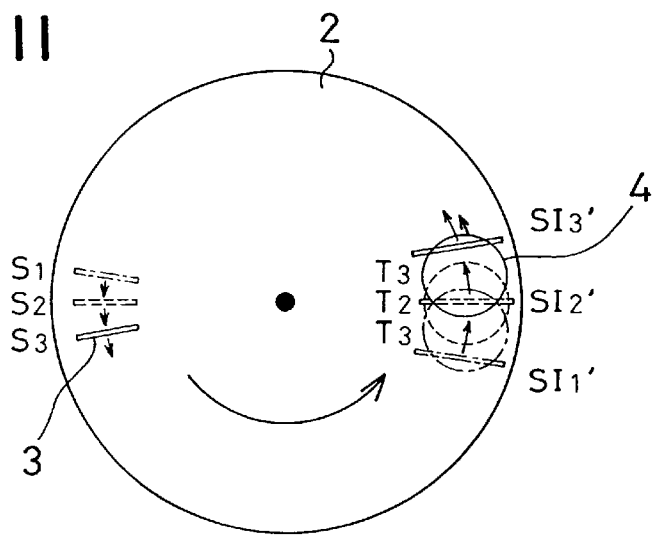
FIG. 11 illustrates the positional relationship between a sample which is arranged in the rotary disk and a slit image which is projected as an inverted image by an optical system such as shown in FIG. 10.

Next, the function of the apparatus shown in FIG. 10 will be described. FIG. 10 shows a state where a beam of illumination light from the light source 1 is transmitted through the slit 3 to be projected as an inverted image of the slit 3 on the sample 5 via the projecting optical system 15. As shown in FIG. 11, in the course that the rotary disk 2 is driven by the motor 6 to rotate counterclockwise (as indicated by the single-headed arrow in FIG. 10), the slit 3 and the sample chamber 4 are shifted counterclockwise in orders of $S_1$, $S_2$, $S_3$ and $T_1$, $T_2$, $T_3$, respectively, while the inverted image of the slit 3 also is shifted counterclockwise in order of $SI_1'$, $SI_2'$, $SI_3'$ because the slit image is directly projected on the sample 5. Since the slit image is projected as an enlarged image to move faster than the sample 5, it sweeps and outpaces the sample 5 in front of the objective lens 13 during rotation of the rotary disk 2.

Figure 14:
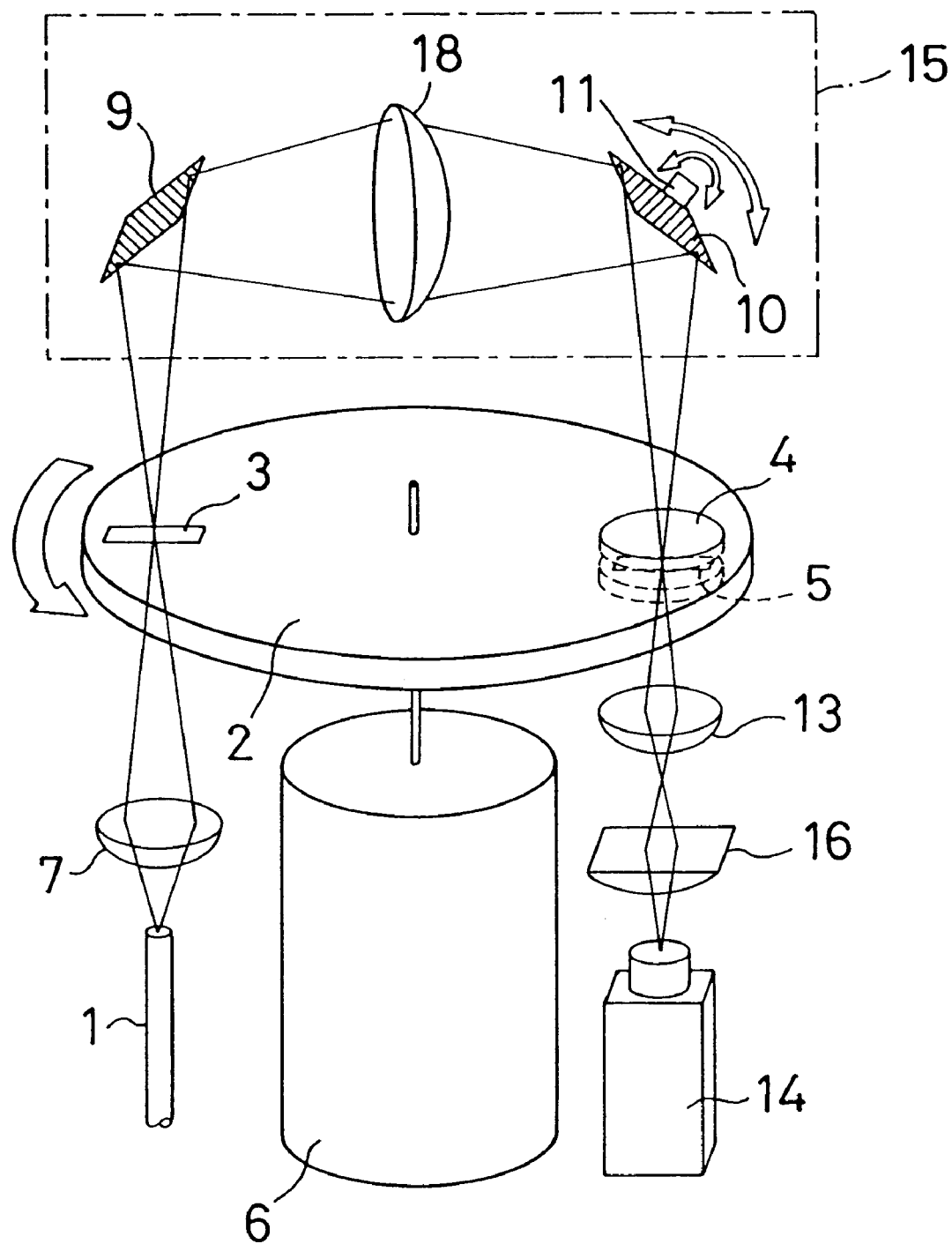
FIG. 14 is an overall view of a modification of the microscope shown in FIG. 10 wherein an anamorphic optical system is employed for correcting the sample image.
Figure 15:
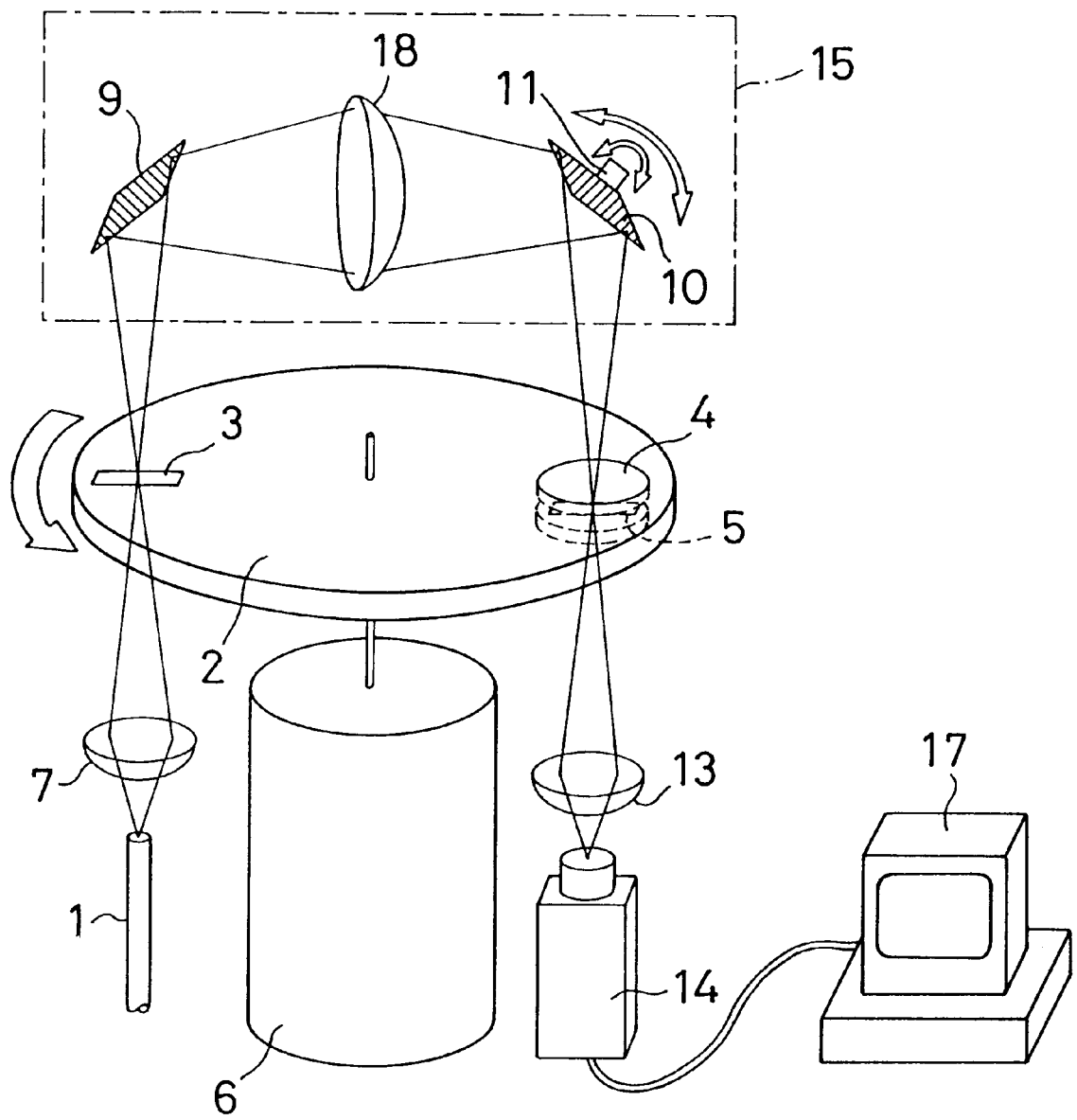
FIG. 15 is an overall view of another modification of the microscope shown in FIG. 10 wherein a means for image processing is added to correct the sample image.

FIG. 12 schematically shows a process in which the slit image and the sample 5 sweep by each other as moving in parallel directions. Time elapses in the order of $t_1$, $t_2$, $t_3$. In this case, a sample image for observation is obtained expanded only in the moving direction of the slit image or the sample 5 (i.e. tangent direction to the rotary disk 2) as shown in FIG. 13A. The degree of expansion depends on the relationship in speed between the slit image and the sample 5. This one-directionally expanded image can be optically transformed to have the original aspect ratio of the sample 5, as shown in FIG. 13B, by an anamorphic optical system 16 which has different powers for X and Y directions and is disposed between the objective lens 13 and the camera 14, as shown in FIG. 14. Alternatively, the sample image may be electrically corrected by an image processor 17 which is connected to the camera 14, as shown in FIG. 15, to be displayed as an appropriate distortion-free image on a video sensor or display.

Each of the above-described embodiments has a configuration in which the slit 3 and the sample 5 are arranged in one rotary disk 2. The present invention, however, is applicable to a case where the slit 3 and the sample chamber 4 are arranged in different rotary disks; a similar effect can be obtained in such a case also.

Figure 16:
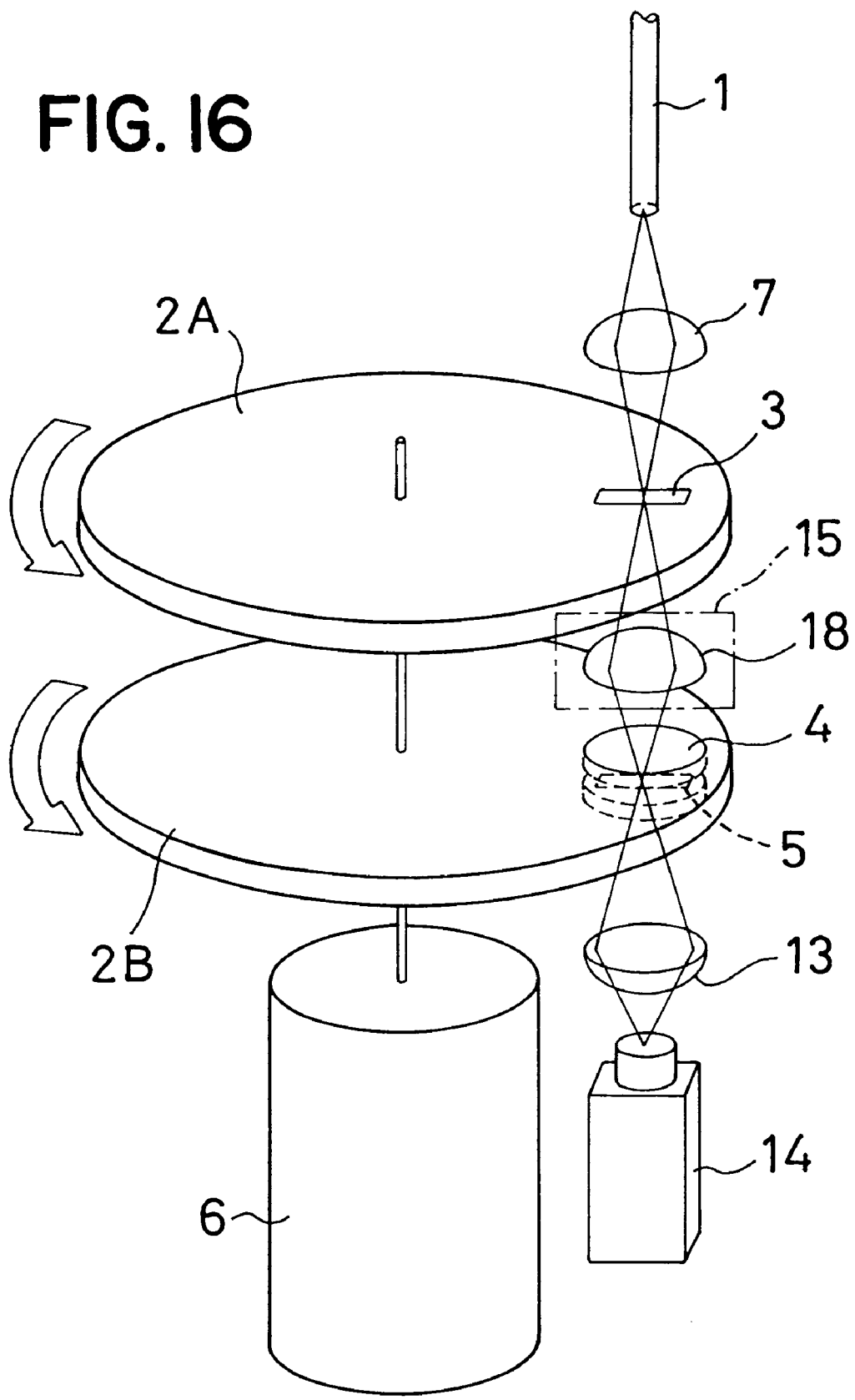
FIG. 16 is an overall view showing an optical system of an inverted-image-mode slit scan centrifuge microscope according to another embodiment of the present invention.

FIG. 16 shows a microscope of one embodiment in this case. According to this embodiment, two rotary disks 2A, 2B are mounted on a rotation axle of a motor 6 upon being appropriately spaced from each other. The rotary disk 2A is provided with a slit 3 and the rotary disk 2B is provided with a sample chamber 4. A projecting optical system 15 is placed between the rotary disks 2A and 2B, to project an image of the slit 3 on a sample 5 which is contained in the sample chamber 4. In this embodiment, the projecting optical system 15 is composed of a lens 18 to project an inverted image of the slit 3 on the sample 5. However, it may be modified such as to project an erect image of the slit 3 by first forming an intermediate image between the rotary disks 2A and 2B, as in the embodiment shown in FIG. 1.

In the embodiment shown in FIG. 16, since the motor 6 rotates the rotary disks 2A, 2B co-axially and integrally to stabilize the high-speed relative movement between the sample 5 and the image of the slit 3, the sample 5 can be observed with good definition as in the above-detailed embodiments.

Figure 17:
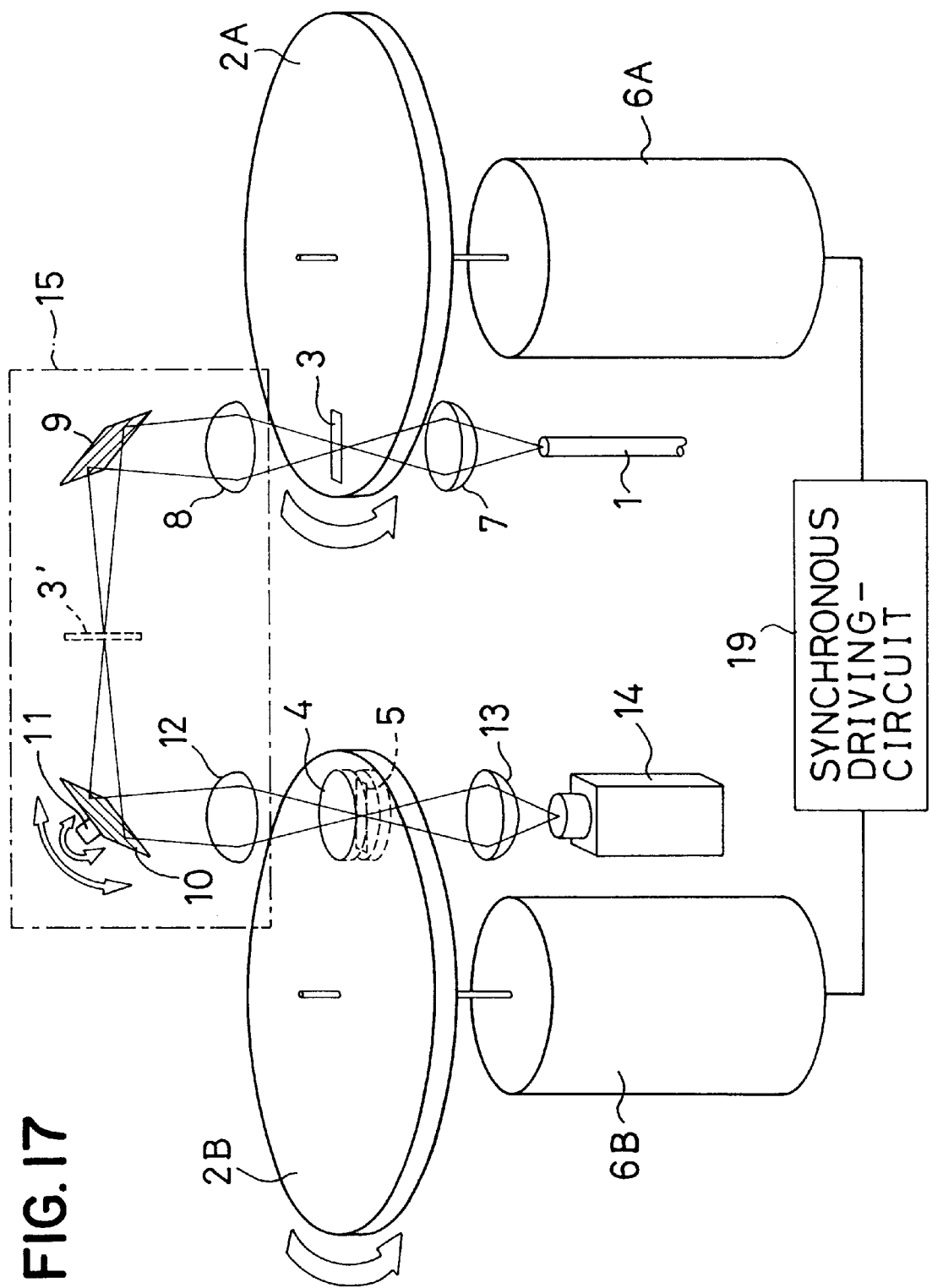
FIG. 17 is an overall view showing an optical system of an erect-image-mode slit scan centrifuge microscope according to another embodiment of the present invention.

FIG. 17 shows another embodiment in the case where the slit 3 and the sample chamber 4 are arranged in different rotary disks. This embodiment is different from the embodiment shown in FIG. 16 in that the rotary disks 2A, 2B are rotated by different motors 6A and 6B, respectively, and in that the projecting optical system 15 is similar to that shown in FIG. 1. The motors 6A, 6B are made to synchronously rotate in parallel directions by a known synchronous driving circuit 19. The embodiment shown in FIG. 17 is similar to the embodiment shown in FIG. 1 in function and effect, and thus detailed description is omitted here.

Figure 18:
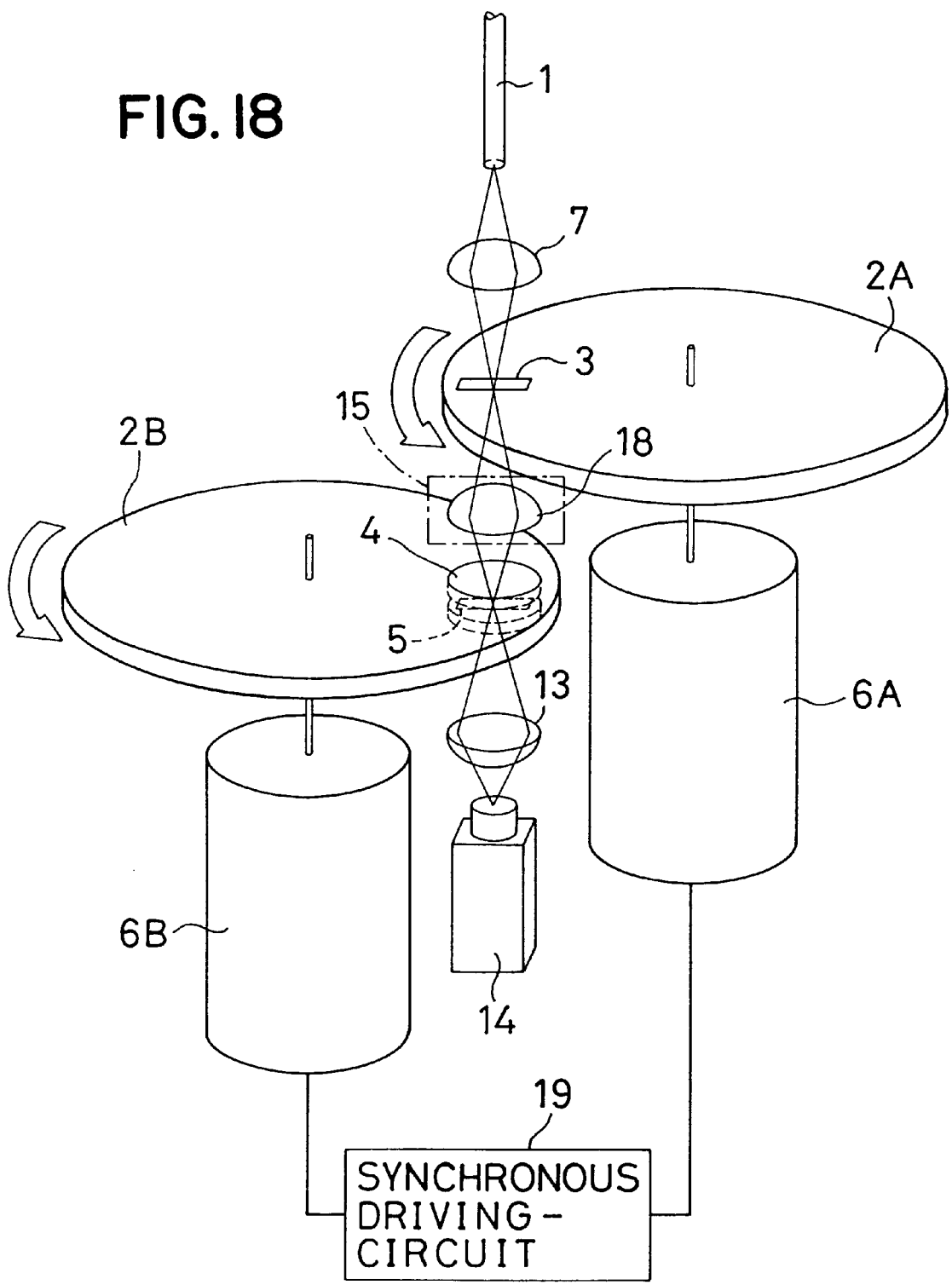
FIG. 18 is an overall view showing an optical system of an inverted-image-mode slit scan centrifuge microscope according to still another embodiment of the present invention.

FIG. 18 shows still another embodiment in the case where the slit 3 and the sample chamber 4 are arranged in different rotary disks. This embodiment is different from the embodiment shown in FIG. 17 in that the projecting optical system 15 projects an inverted image of the slit 3 on the sample 5 in the sample chamber 4. The embodiment shown in FIG. 18 is similar to the embodiment shown in FIG. 16 in function and effect, and thus detailed description is omitted here.

In the embodiments shown in FIGS. 16–18, the rotary disks 2A and 2B rotate in parallel directions. They, however, may be constructed and arranged to rotate in mutually opposite directions.

The foregoing descriptions relate to several embodiments of the centrifuge microscope according to the present invention. By incorporating various optical elements used in conventional optical microscopes into such a centrifuge microscope, dark field-, fluorescence-, polarization-, phase contrast- and differential interference- observations are available under centrifugal force. While the sample embodiments are based on the use of inverted microscopes, they are equally applicable to use on upright microscopes.

What is claimed is:

1. A centrifuge microscopes comprising:

a light source;

a slit arranged in a beam of light emergent from said light source;

an objective lens;

a first rotary disk provided with a sample chamber, said sample chamber being arranged such as to cross an optical axis of said objective lens in accordance with rotation of said first rotary disk; and a projecting optical system for projecting the beam of light transmitted through said slit on a sample contained in said sample chamber as a slit image, wherein, when the sample is carried in front of said objective lens during rotation of said first rotary disk, the slit image projected by said projecting optical system is moving to change a position thereof with respect to the sample.

2. A centrifuge microscope comprising:

a light source;

a slit arranged in a beam of light emergent from said light source;

an objective lens;

a first rotary disk provided with a sample chamber, said sample chamber being arranged such as to cross an optical axis of said objective lens in accordance with rotation of said first rotary disk, and a projecting optical system for projecting the beam of light transmitted through said slit on a sample contained in said sample chamber as a slit image, wherein, when the sample is carried in front of said objective lens during rotation of aid first rotary disk, the slit image projected by said projecting optical system is changing a position thereof with respect to the sample, and wherein said slit is arranged in said first rotary disk.

3. A centrifuge microscope comprising:

a light source;

a slit arranged in a beam of light emergent from said light source;

an objective lens;

a first rotary disk provided with a sample chamber, said sample chamber being arranged such as to cross an optical axis of said objective lens in accordance with rotation of said first rotary disk;

a second rotary disk; and a projecting optical system for projecting the beam of light transmitted through said slit on a sample contained in said sample chamber as a slit image, wherein, when the sample is carried in front of said objective lens during rotation of said first rotary disk, the slit image projected by said projecting optical system is changing a position thereof with respect to the sample, and wherein said slit is arranged in said second rotary disk.

4. A centrifuge microscope, a light source;

a slit arranged in a beam of light emergent from said light source;

an objective lens;

a first rotary disk provided with a sample chamber, said sample chamber being arranged such as to cross an optical axis of said objective lens in accordance with rotation of said first rotary disk;

a second rotary disk; and a projecting optical system for projecting the beam of light transmitted through said slit on a sample contained in said sample chamber as a slit image, wherein, when the sample is carried in front of said objective lens during rotation of said first rotary disk, the slit image projected by said projecting optical system is changing a position thereof with respect to the sample, and wherein said slit is arranged in said second rotary disk, wherein said first rotary disk and said second rotary disk are rotated by one driving unit.

5. A centrifuge microscope according to claim 3, wherein said first rotary disk and said second rotary disk are rotated by two different driving units, respectively, said driving units being synchronized by a synchronizer.

6. A centrifuge microscope according to claims 2, 4 or 5, wherein said slit image and said sample are moved in mutually opposite directions to sweep by one another in front of said objective lens.

7. A centrifuge microscope according to claim 6, wherein said projecting optical system is constructed such that said slit image on the sample is a full-scale image.

8. A centrifuge microscope according to claim 6, wherein said projecting optical system is constructed such that said slit image on the sample is an enlarged image.

9. A centrifuge microscope according to claims 2, 4 or 5, wherein said slit image and said sample are moved in parallel directions to sweep by one another in front of said objective lens.

10. A centrifuge microscope according to claim 9, wherein said projecting optical system is constructed such that said slit image on the sample is an enlarged image.

11. A centrifuge microscope according to claims 2 or 5, wherein said projecting optical system includes at least one reflecting mirror, said slit image being projected on the sample via said reflecting mirror.

12. A centrifuge microscope according to claim 11, wherein said reflecting mirror is provided with adjusting means for adjusting a position of said slit image.

13. A centrifuge microscope comprising:

a light source;

a slit arranged in a beam of light emergent from said light source;

an objective lens;

a first rotary disk provided with a sample chamber, said sample chamber being arranged such as to cross an optical axis of said objective lens in accordance with rotation of said first rotary disk; and a projecting optical system for projecting the beam of light transmitted through said slit on a sample contained in said sample chamber as a slit image, wherein, when the sample is carried in front of said objective lens during rotation of said first rotary disk, the slit image projected by said projecting optical system is changing a position thereof with respect to the sample, and wherein said slit image and said sample are moved in mutually opposite directions to sweep by one another in front of said objective lens.

14. A centrifuge microscope according to claim 13, wherein said projecting optical system is constructed such that said slit image on the sample is a full-scale image.

15. A centrifuge microscope according to claim 13, wherein said projecting optical system is constructed such that said slit image on the sample is an enlarged image.

16. A centrifuge microscope comprising:

a light source;

a slit arranged in a beam of light emergent from said light source;

an objective lens;

a first rotary disk provided with a sample chamber, said sample chamber being arranged such as to cross an optical axis of said objective lens in accordance with rotation of said first rotary disk; and a projecting optical system for projecting the beam of light transmitted through said slit on a sample contained in said sample chamber as a slit image, wherein when the sample is carried in front of said objective lens during rotation of said first rotary disk, the slit image projected by said projecting optical system is changing a position thereof with respect to the sample, and wherein said slit image and said sample are moved in parallel directions to sweep by one another in front of said objective lens.

17. A centrifuge microscope according to claim 16, wherein said projecting optical system is constructed such that said slit image on the sample is an enlarged image.

* * * * *